United States Patent [19]

Basoglu et al.

[11] Patent Number: 5,528,302
[45] Date of Patent: Jun. 18, 1996

[54] REAL-TIME ULTRASOUND SCAN CONVERSION

[75] Inventors: Christopher H. Basoglu, Bothell; Yongmin Kim, Seattle, both of Wash.

[73] Assignee: University of Washington, Seattle, Wash.

[21] Appl. No.: 521,783

[22] Filed: Aug. 31, 1995

[51] Int. Cl.$^6$ .................................................. H04N 7/01
[52] U.S. Cl. .................................. 348/442; 348/163
[58] Field of Search .................................. 348/163, 162, 348/442, 440; 128/660.01; H04N 7/01, 11/02, 5/31

[56] References Cited

U.S. PATENT DOCUMENTS

| | | | |
|---|---|---|---|
| 4,245,250 | 1/1981 | Tiemann | 348/163 |
| 4,386,528 | 6/1983 | Engle. | |
| 4,468,747 | 8/1984 | Leavitt et al. | 348/163 |
| 4,471,449 | 9/1984 | Leavitt et al. | 348/163 |
| 4,581,636 | 4/1986 | Blaker et al.. | |
| 4,618,887 | 10/1986 | Birk | 348/442 |
| 4,689,675 | 8/1987 | Tchorbajian et al. | 348/163 |
| 4,703,440 | 10/1987 | Birk et al. | 348/163 |
| 4,719,509 | 1/1988 | Sakamoto | 348/163 |

Primary Examiner—Safet Metjahic
Assistant Examiner—Michael H. Lee
Attorney, Agent, or Firm—Steven P. Koda

[57] ABSTRACT

A scan conversion method is implemented to achieve real-time scan conversion at video rates. Scan conversion tasks include vector point identification processing, distance derivation processing and interpolation processing. An active image area is defined in response to user inputs. For a given set of user adjustments there is a fixed active image area of the display screen. In addition, there is a fixed positional relationship between output pixel locations of the active image and corresponding input vector points of the active image. Whenever the user makes adjustments, these relationships change becoming fixed again until another user-initiated change. Whenever the relationships change, vector identification processing and distance derivation processing is re-done to define these relationships. Interpolation processing is performed each frame only for output pixels within the active image area. The active image area is divided into groups of output pixels. For a given group of output pixels, a parallel processor receives the pre-computed data and input vector data. The parallel processor then interpolates the vector data samples for each output pixel in the group.

4 Claims, 11 Drawing Sheets

REAL-TIME ULTRASOUND SCAN CONVERSION

BACKGROUND OF THE INVENTION

This invention relates to ultrasound medical imaging systems, and more particularly to real-time scan conversion methods in an ultrasound system.

Ultrasound medical imaging is the imaging of internal areas of a patient's body using ultrasound energy. Ultrasound energy is sound wave energy having a frequency greater than approximately 20 kHz. Ultrasound signals, typically of 2 MHz to 10 MHz, are transmitted into a patient's body via a transducer array. The signals are in-part absorbed, dispersed, refracted and reflected by the patient's body. Reflected ultrasound signals are received at transducer elements which convert the reflected ultrasound signals back into electronic signals. A received ultrasound beam-pattern is a product of the transmit beam-pattern and the reflected beam-pattern. The received beam-pattern typically is processed to analyze echo, doppler and flow information and obtain an image of the patient's encountered anatomy (e.g., tissue, flow, doppler).

Typically, ultrasound energy is directed in a sector scan of a patient area. In such instances, the received beam-pattern is a group of polar-coordinate vectors. As the display devices are raster cartesian-coordinate devices, the received data is converted into raster format. Such conversion is referred to as a scan conversion process. It also is known to direct ultrasound energy as a linear scan of a patient's area. In such case, the received beam-pattern is a group of cartesian-coordinate vectors. As the display devices are raster cartesian-coordinate devices, the received data is converted and/or scaled into a display raster cartesian-coordinate system. Such conversion/scaling also is referred to as a scan conversion process.

Scan conversion involves interpolation and scaling of vector data (e.g., polar or cartesian vectors) into raster data. A resulting set of raster data is used to define an ultrasound display image at a given moment in time. Multiple sets of raster data are used to (i) define the same image at different times, or (ii) add a third dimension to an image. Conventional ultrasound imaging systems allow display of an image as a sector area or a cartesian grid. The scan conversion process manipulates collected data to generate raster image data in a desired display format. It also is known to geometrically transform the vector data to zoom in on or rotate an image.

The classical scan conversion method is to work back from a raster point on the display. For a given raster point, an inverse transformation is performed to identify input vector samples in the vicinity of the raster point. As the collected input data is a set of vectors, the output raster point does not exactly coincide with a given input vector. Thus, nearby input vectors are identified, then the values for such vectors are interpolated to define a value at the raster point of interest. Such process is performed for each raster point on the display. As a result, the scan conversion process is computation intensive.

It is desirable to reduce computation overhead or otherwise increase efficiency in allocating system throughput for an ultrasound system. Accordingly, it is desirable to achieve an efficient scan conversion method.

SUMMARY OF THE INVENTION

According to the invention, an efficient scan conversion method is implemented by reducing processing overhead, by efficiently handling data and by processing pixel data in parallel. During the scan conversion process, pixel output data is derived from input ultrasound vector data. Each output pixel value is derived by interpolating a determined set of input vector data samples. Input vector data points of interest are identified for each output pixel location. Offset distances weights are calculated between each input vector sample of interest and a given output pixel location. The scan conversion tasks are organized into vector point identification processing, distance derivation processing and interpolation processing.

According to one aspect of the invention, processing overhead is reduced by identifying an active image area on the display. The display screen includes an active image area and a background area. The ultrasound image is displayed in the active image area. Text or other background information is displayed in the background area. The active image area is defined based upon user inputs for ultrasound image size, shape, focus and steering. For a given set of user adjustments the active image area is fixed. In addition, the positional relationship between output pixel locations within the active image area and corresponding input vector points of the active image are fixed. Thus, the distance weights are fixed. Such area, positional relationships and distance weights remain valid and fixed until the user makes adjustments. When the user makes adjustments, the image area, positional relationships and/or distance weights may change, becoming fixed again until another user-initiated change. Processing overhead is reduced by performing vector identification processing and distance derivation processing only when the user makes adjustments affecting the active image area, positional relationships or distance weights.

Conventionally, every output pixel is tested every frame to determine whether it is within an active pixel area. Such testing involves deriving a polar coordinate point corresponding to the output pixel, then comparing the point location to the input vector sample locations. Deriving the polar coordinate point is computation intensive involving nearest neighbor and square root calculations. Such testing is avoided, here by performing vector identification processing and distance derivation processing only when the user makes adjustments affecting the active image area, positional relationships or distance weights.

According to another aspect of the invention, interpolation processing then is performed each frame only for output pixels within the active image area.

According to another aspect of the invention, the active image area is divided into groups of output pixels. A given parallel processor performs interpolation on one group at a time. For multiple parallel processor embodiments, the groups of pixels are allocated among the processors. For example, in a four parallel processor embodiment and an image area formed by 1000 groups, each processor is allocated 250 groups (i.e., one-fourth of the active image area).

According to another aspect of the invention, for a given group of output pixels, a parallel processor receives sets of pre-computed offset distance weights for each output pixel. In addition, vector data samples for vector locations corresponding to output pixel are loaded. The parallel processor then interpolates the vector data samples for each output pixel in the group using the sets of distance weights. In one embodiment the offset distance weights include a range offset and a vector offset component for each vector location. In one embodiment, an interpolation kernel of n×m vectors is used for each output pixel. Exemplary kernels include 2×2, 2×4 and 4×4 vector samples.

According to another aspect of the invention, a data transfer controller loads vector sample data and offset distance weights into local memory for a parallel processor. The parallel processor's local memory includes multiple buffers. Two buffers are accessed in ping-pong fashion for processing pixel groups. During a first loop, the parallel processor performs interpolation for data stored in the first buffer while the transfer controller loads the second buffer with data for the next group. During the next loop, the parallel processor performs interpolation for data stored in the second buffer, while the transfer controller loads the first buffer. A third buffer is loaded by the transfer controller with the offset distance weights used during interpolation.

One advantage of the scan conversion method of this invention is that a fast, efficient scan conversion occurs. Specifically, the complex nearest neighbor and square root functions executed for vector identification tasks are isolated from the interpolation tasks. Another advantage is that processing is reduced by avoiding interpolation for background points. Processing also is reduced by not having to perform blanking and bound checking for every pixel.

These and other aspects and advantages of the invention will be better understood by reference to the following detailed description taken in conjunction with the accompanying drawings.

BRIEF DESCRIPTION OF THE DRAWINGS

FIG. 1 is a diagram of ultrasound input vectors oriented relative to an ultrasound transducer;

FIGS. 2a–c are diagrams of vector sample storage, vector sample display without scan conversion and vector sample display with scan conversion;

DESCRIPTION OF SPECIFIC EMBODIMENTS

Scan Conversion Overview

Figures 1, 2A, 2B, 2C:
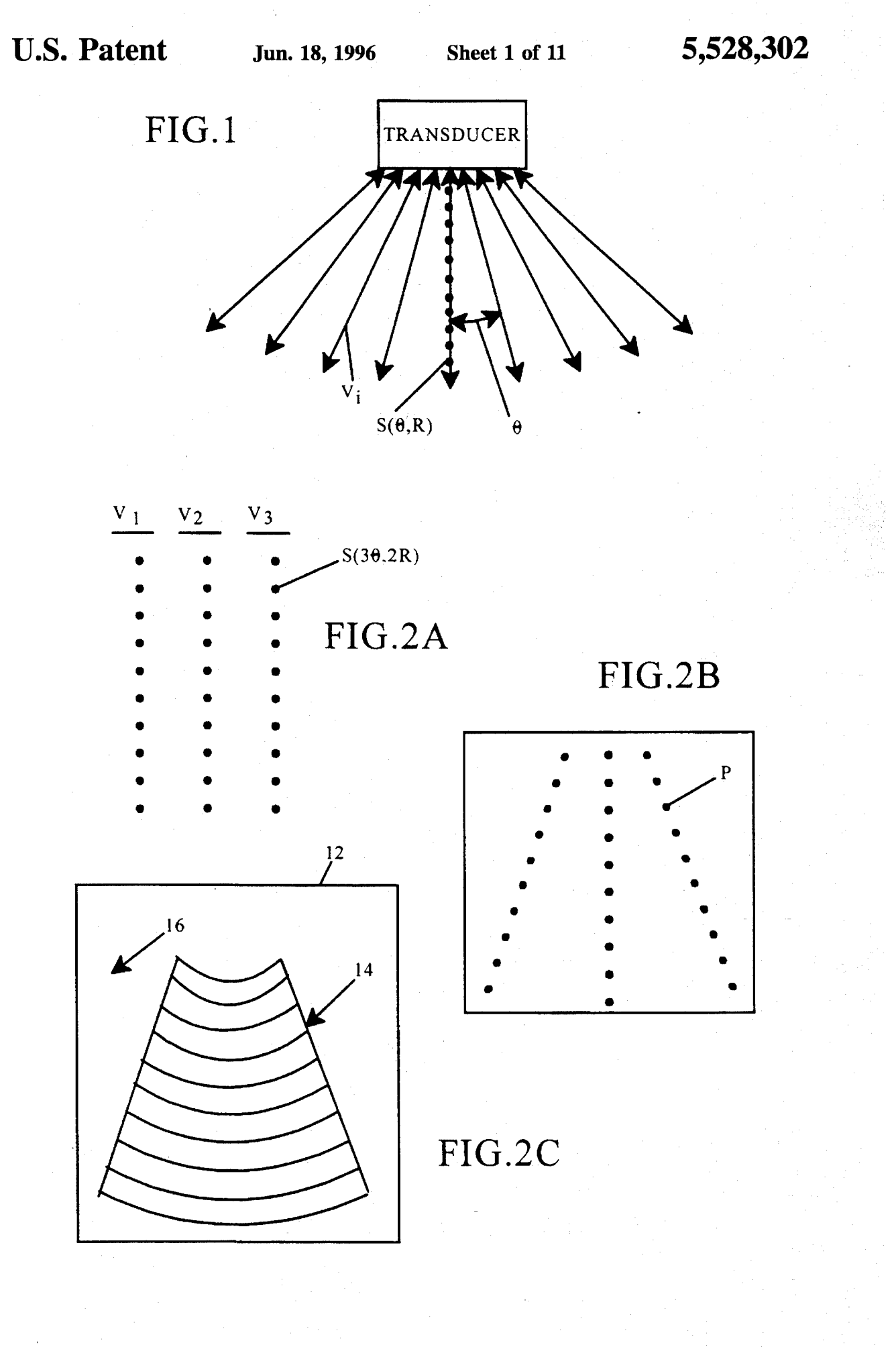
Figure 3:
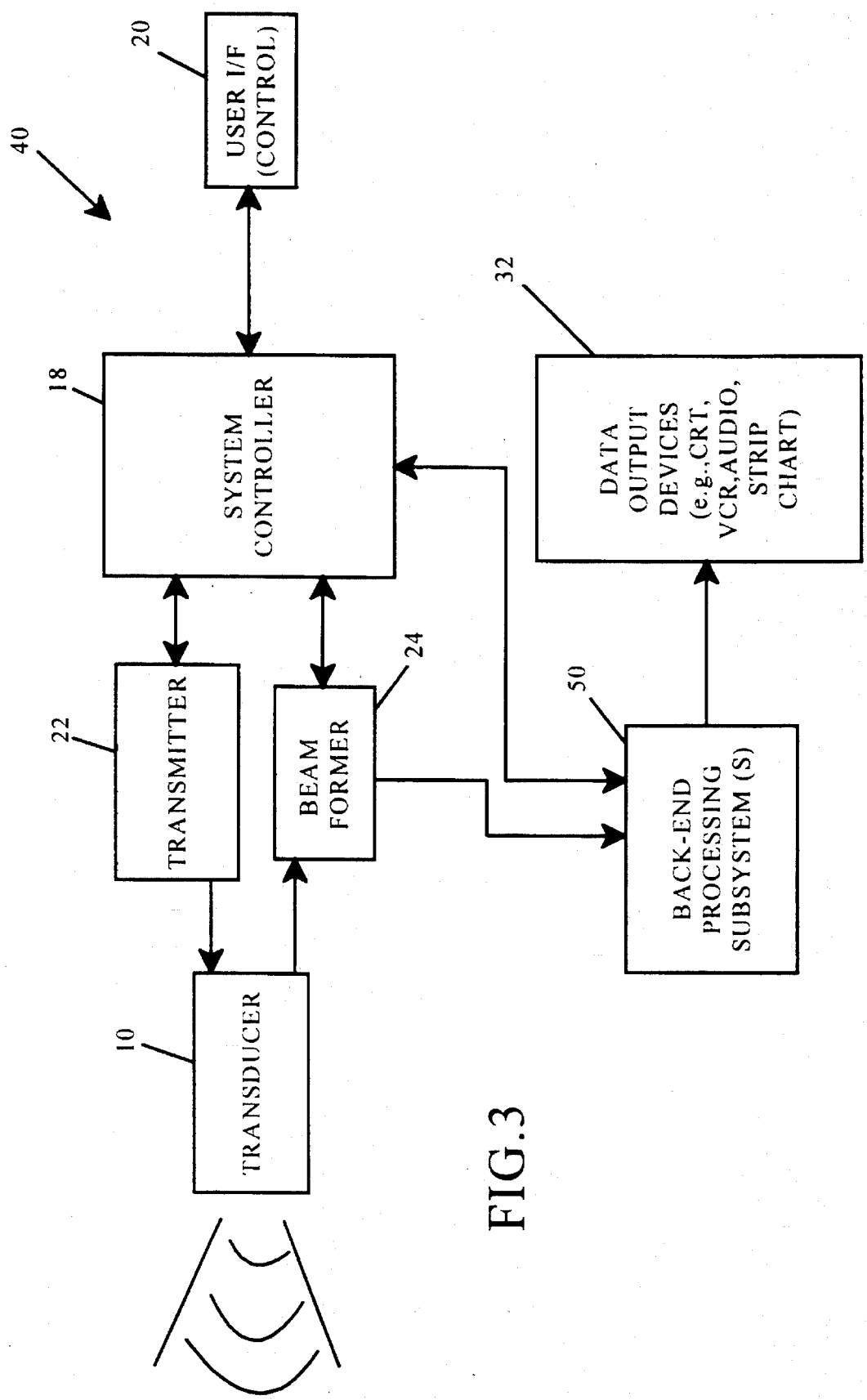
FIG. 3 is a block diagram of an ultrasound medical diagnostic imaging system.

An ultrasound image is generated by collecting a number of co-planar acoustic signals. These signals are filtered and beam-formed resulting in a set of digital input vectors V. FIG. 1 shows a transducer 10 which transmits ultrasound signals and receives ultrasound echoes modelled as a collection of input vectors $V_i$. Each vector has an angular orientation relative to the transducer 10 face. The angle between successive vectors typically is the same, $\theta$. Each vector is stored as discrete samples S. In one embodiment each sample is defined in polar coordinates as a function of angle ($\theta$) and of radius (R). Typically, there are 250–800 input vectors and 250–1000 samples per vector.

During operation, a transducer scans a patient area in sector fashion resulting in multiple ultrasound input vectors, $V_i$. FIG. 2a depicts vector storage as an array of vector points $S(\theta,R)$. For an embodiment of 250 vectors by 250 samples/vector there are 62500 vector data points S. These vector points are used to derive a display image. The display screen is formed by a raster of pixels. To achieve an image the vector points are transformed to raster output pixels. Typically, the number of input vector points is much less than the number of output pixels. Thus, to obtain a smooth aesthetically-pleasing, yet accurate image, pixel data is interpolated or otherwise derived from the pattern of input vector values. For conventional imaging, the values are gray-scale values, although color values from a color palette also can be used. The conversion process is referred to as scan conversion. Scan conversion also encompasses zoom, size and shape functions (i.e., any geometric transformation of input vector samples).

FIG. 2b shows corresponding pixel locations for an image without scan conversion. For the locations of FIG. 2b, there is a one-to-one correspondence between vector points S and display pixels P. (Note that FIG. 2b shows pixel location not pixel value. A display of pixel values would appear similar, but at each location a gray-scale light intensity would be present). FIG. 2c depicts interpolation of additional pixels to achieve additional image resolution. Note that in FIG. 2c a display screen 12 includes an active image area 14 and a background image area 16. The active image area is the portion of the screen 12 where the ultrasound sector scan image appears. The background portion 16 is the remaining area.

Following are descriptions of a host ultrasound medical diagnostic system, and a scan conversion apparatus and scan conversion method according to embodiments of this invention.

Ultrasound Medical Diagnostic Host

FIG. 3 shows a block diagram of an ultrasound medical diagnostic imaging system 40. The function of the system 40 is to perform diagnostic imaging of a patient using ultrasound data. Ultrasound signals are transmitted via transducer 10 into a patient. Reflected signals are detected and used to derive internal images of the patient for a scanned area/volume.

A system controller 18 receives and displays user control information via a user interface 20. During operation, system control signals are output to an ultrasound front end (i.e., transducer 10, transmitter 22, beam-former 24 and related circuitry) and to various subsystems. A transmitter 22 generates output signals to a transducer 10 to define aperture, apodization, focus and steering of ultrasound signals. The transducer 10 is an array of transducer elements. The elements define multiple channels, each channel for transmitting and/or receiving ultrasound signals. Transmitted ultrasound signals are in part absorbed, dispersed, refracted and reflected when travelling through a patient. Reflected signals are sensed by the transducer 10 and captured as a patterned beam by beam-former 24. The captured signals are sent to one or more back-end processing subsystems 50. The function of back-end processing subsystem(s) 50 is to process the raw beam data and generate image data for output devices 32.

Figure 4:
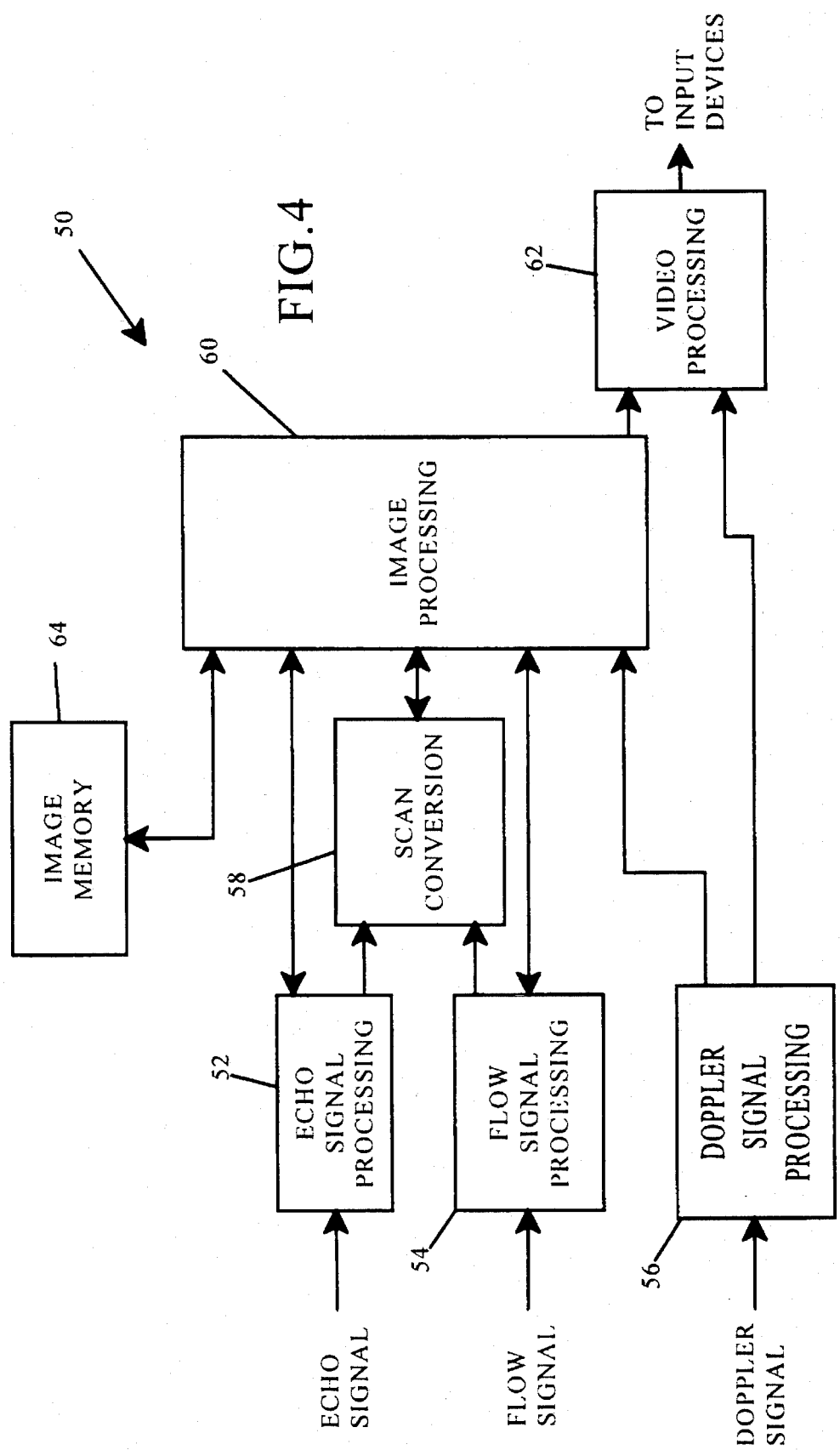
FIG. 4 is a functional block diagram of the back-end processing subsystem(s) of FIG. 3.

FIG. 4 is a block diagram of back-end processing functions. Digital echo signals, flow signals and/or doppler signals are received at the back-end processing subsystem(s) 50 according to various modes of operation. Such input signals are referred to herein as vector signals. For a transducer 10 performing sector scanning, the vector signals are digital polar-coordinate data samples of echo, flow and/or doppler signals. For a transducer 10 performing linear scanning, the vector signals are digital cartesian-coordinate data samples of echo, flow and/or doppler signals.

Back-end processing includes echo signal processing 52, flow signal processing 54, doppler signal processing 56, scan conversion 58, image processing 60 and video processing 62. Echo signal processing 52 typically encompasses signal enhancement filtering, energy detection and image enhancement filtering. Various filtering and convolution techniques are employed. The purpose of echo signal processing 52 is to enhance the signal to noise ratio of the echo signal. Flow signal processing 54 analyzes signals for flow parameters. Typical parameter derivations include sample correlation and flow averaging. The purpose of flow signal processing 54 is to identify flow and turbulence within a scanned area. Doppler signal processing 56 typically encompasses signal enhancement filtering, spectral estimation processing, energy detection, and derived waveform filtering. The purpose of doppler signal processing 56 is to identify and filter out doppler shift, to improve spectral frequency response and to coordinate spectral mapping.

A scan conversion process 58 converts the processed vector data streams from echo signal processing 52 and flow signal processing 54. For polar-coordinate vector data the data is converted into cartesian-coordinate raster data. For cartesian-coordinate vector data the data is scaled into cartesian-coordinate raster data.

Image processing 60 includes image enhancement processes executed on the raster data or vector data. In an off-line delayed playback (e.g., cine playback) mode of operation image data, vector data and/or raster data is received from image memory 64 and processed.

Video processing 62 executes on the image processed data to generate video signals, audio signals, and graphing signals for output to a display device, audio device, storage device (e.g., VCR) and/or charting device. Video processing 62 in some applications also executes on doppler processed vector data to generate similar video signals, audio signals, and graphing signals for output to the display device, audio device, storage device and/or charting device.

Scan Conversion Apparatus

Figure 5:
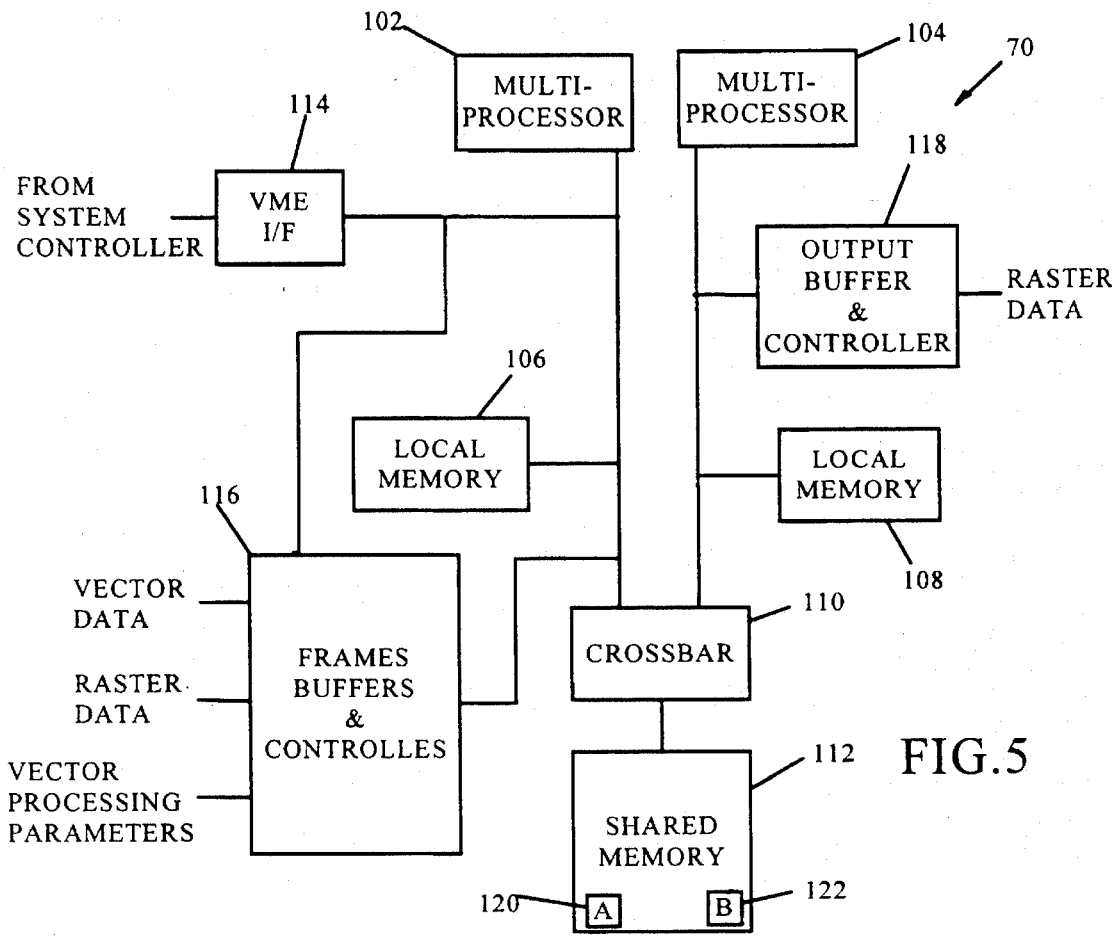
FIG. 5 is a block diagram of a scan conversion apparatus for performing the scan conversion function of FIG. 4.

FIG. 5 shows a block diagram of a scan conversion apparatus 70 for performing the scan conversion function 58 according to one embodiment of this invention. Apparatus 70 includes one or more processors. In a specific embodiment a pair of processors 102, 104 are included. The apparatus 70 also includes local memory 106, 108, crossbar switch 110, shared memory 112, modified-VME interface 114, frame buffer/controller 116 and output buffer/controller 118.

Processors

Figure 6:
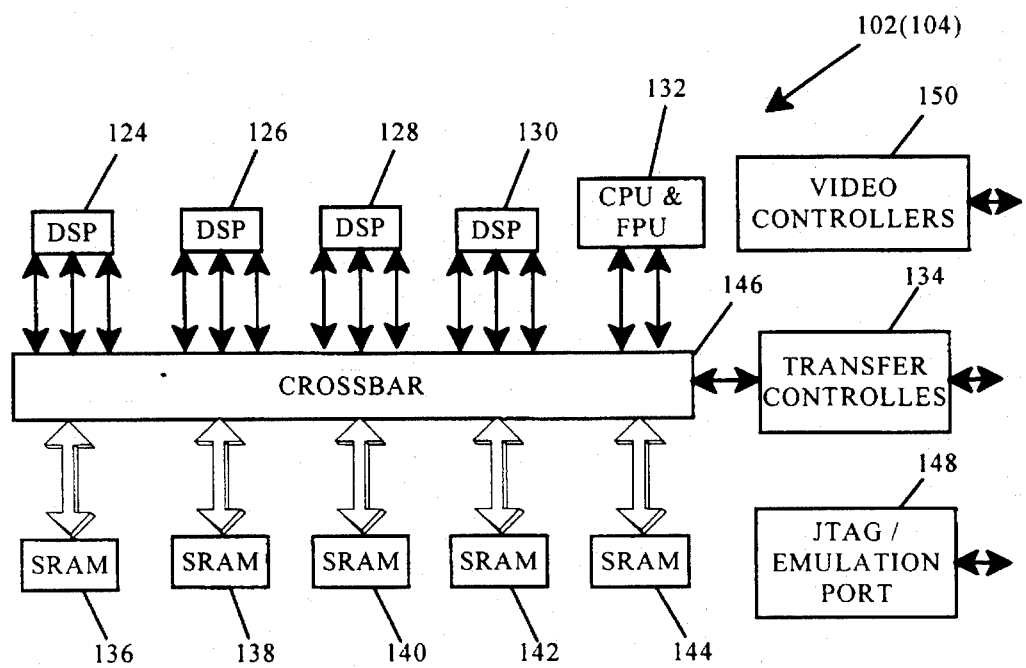
FIG. 6 is a block diagram for one embodiment of a multi-processor of FIG. 5.

In one embodiment each processor 102, 104 includes one or more digital signal processors. In a specific embodiment each processor 102, 104 is a multi-processor, such as a Texas Instruments multimedia video processor ("MVP") (part no. TMS320C80). FIG. 6 shows a block diagram of an MVP multi-processor. The MVP combines on a single semiconductor chip, four fully programmable digital signal processors 124, 126, 128, 130 and a master processor 132 for handling multiple data streams via a transfer controller 134. Several on-chip random access memory (RAM) devices 136, 138, 140, 142, 144 serve as resident memory accessible to the digital signal processors (DSPs) 124–130 via a crossbar network 146. The MVP has a throughput rating of approximately 2 billion operations per second. The master processor 132 is a RISC processor with an integral floating point unit. According to this embodiment the master processor 132 coordinates and distributes processing tasks among the DSPs 124–130 and manages external off-chip communications. A JTAG/emulation port 148 is included for aid in testing, development and diagnostics.

Each DSP 124–130 includes two address generators, three input 32-bit ALUs, a 16×16 multiplier, three zero-overhead loop controllers, and a 32-bit barrel shifter. Each RAM 136–144 has a 10 kB capacity providing 50 kB of single-cycle SRAM. Memory 136–144 is partitioned in blocks with each block serving as either data RAM, parameter RAM, data cache or instruction cache. The data caches and instruction caches serve as a primary cache. The transfer controller 134 services the on-chip caches and interfaces to external memory (e.g., local memory 106 or 108, and shared memory 112).

The MVP also includes a pair of video controllers 150. Controllers 150 generate video synchronization signals or synchronize data transfer rates with external video signals.

Local Memory, Shared Memory, Crossbar

Referring again to FIG. 5, each multi-processor 102, 104 has a respective dedicated local memory 106, 108, serving as a secondary cache. Each local memory 102, 104 has capacity for storing a frame of ultrasound data. In one embodiment a 2 MB capacity is provided at each local memory 102, 104. In addition shared memory 112 is included. In one embodiment shared memory 112 is implemented as two separate 64 MB memory banks 120, 122 for a total of 128 MB shared memory. The storage capacity of local memory 102, 104 and shared memory 112 varies for alternative embodiments. The multi-processors 102, 104 access shared memory through crossbar switch 110. For a two multi-processor embodiment, a 2×2 crossbar switch is implemented. The purpose of the crossbar switch 110 is to allow the multiple processors 102, 104 simultaneous access to the shared memory banks. The crossbar switch 110 includes a pair of transceivers for each input channel, along with a crossbar controller.

The function of the crossbar controller is (i) to manage requests for access and (ii) to refresh shared memory 112. If a multi-processor 102 requests access to a shared memory bank 120, 122 not currently being accessed by the other multi-processor 104, then the access is granted. If the multi-processor 102 requests access to a shared memory bank 120, 122 currently being accessed, then the multi-processor 102 waits until the memory bank is available. Simultaneous access to a shared memory bank 120, 122 thus is available when the accesses are to separate memory banks. For reconciling simultaneous requests for access, one multi-processor 102 is prescribed to have priority for a specific one shared memory bank 120, while the other multi-processor 104 is prescribed priority for the other shared memory bank 122. If both multi-processors 102, 104 request access to a common bank, then the processor with the prescribed priority for that bank is granted access. However, to avoid lengthy delays, the other multi-processor is granted access after the current access, even if the higher priority multi-processor comes right back with a second request. For example, consider the case in which multi-processor 102 has the prescribed priority to the first memory bank 120. The first multi-processor 102 makes two sequential requests for access to bank 120, while multi-processor 104 also makes a request to bank 120. Because of the prescribed priority, the first multi-processor 102 is granted access for its first request. Next, however, the second multi-processor 104 is granted access. Then, the first multi-processor 102 is granted access for its second request.

Modified-VME Interface

System control signals are received by apparatus 70 from the system controller 18 via a modified-VME interface 114. The modified-VME interface 114 is similar to a standard VME interface, but with a different connector size so as to fit into an ultrasound system 40 back-plane. The communication protocol is VME standard with unnecessary signals not being supported. In an alternative embodiment a standard VME interface is used.

The modified-VME interface includes a back-plane interface, an external address decoder/controller, an interrupt requester, an internal address decoder/controller and dual port memory. The back-plane interface couples the apparatus 70 to a system 40 bus enabling communication with the system controller 18. System data and control signals are received via the back-plane interface and stored in the dual-port memory based upon address decoding and interrupt-based handshaking. Dual port memory has a receive buffer and a transmit buffer. In a specific embodiment the dual port memory is a 2K×16 dual port RAM. Processor bus transceivers isolate the multi-processor 102, 104 address and data busses from the system bus.

For data flow from the system controller 18 into the apparatus 70, the system controller 18 writes data into the transmit buffer. The system controller 18 then signals the VME interrupt requester, which in turn generates an interrupt to the first multi-processor 102. Multi-processor 102 reads the transmit buffer, then signals the VME interface to generate an interrupt to the system controller 18 signifying that the transmit buffer is available for loading.

Data flow from the apparatus 70 to the system controller 18 is similarly controlled. Multi-processor 102 writes data into the receive buffer, then signals the VME interrupt requester to generate an interrupt to the system controller 18. The system controller 18 reads from the receive buffer, then signals the VME interrupt requester to interrupt multi-processor 102 to signify that the receive buffer is available for loading.

Frame Buffer/Controller

Figure 7:
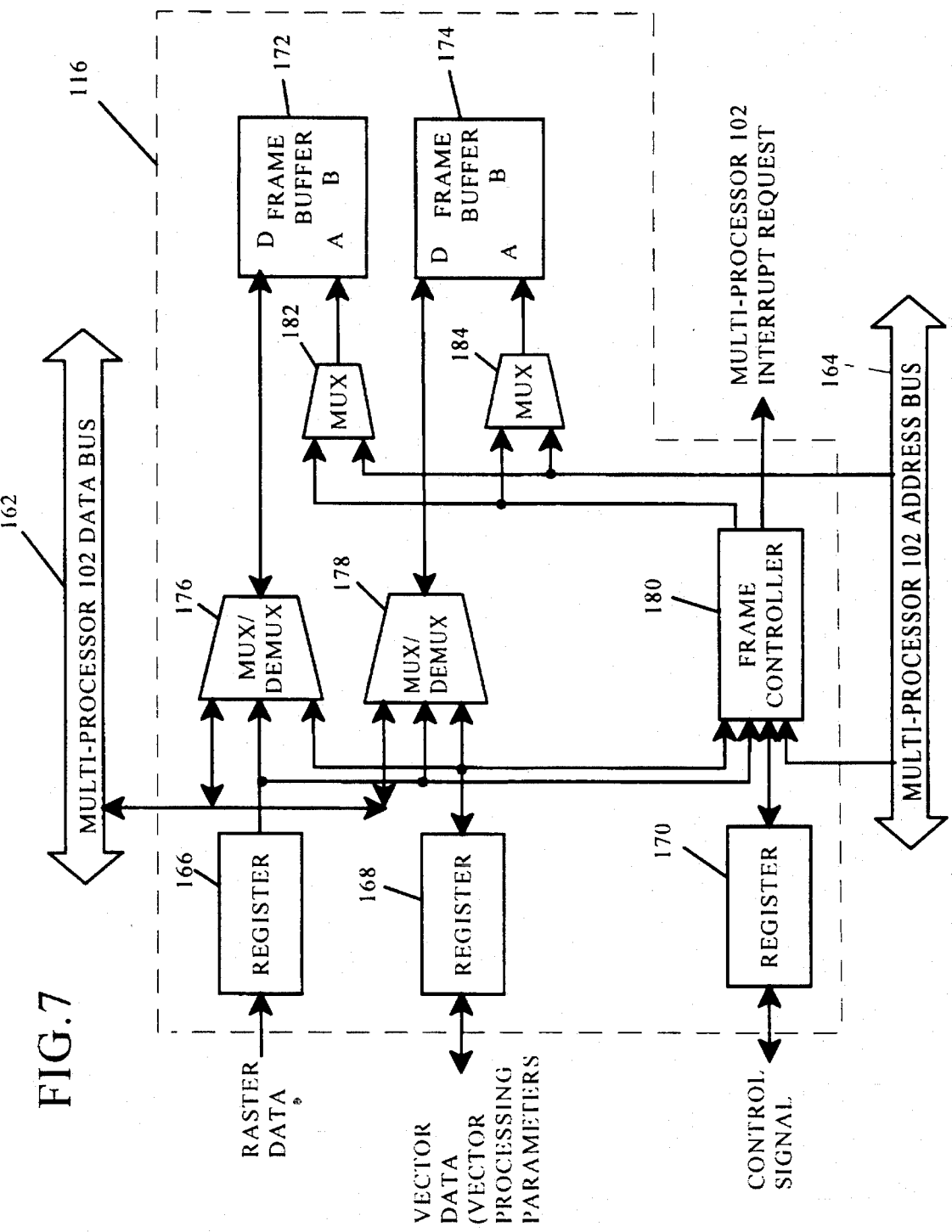
FIG. 7 is a diagram of the input frame buffers of FIG. 5.

The frame buffer/controller 116 serves as a data interface with an ultrasound front end, another programmable ultrasound signal processing apparatus 70, another back-end processing subsystem and/or image memory 64. FIG. 7 shows a block diagram of the frame buffer/controller 116. For an input operation, the frame buffer/controller 116 receives vector data or raster data. Multi-processor 102 then reads the data via a data bus 162 and address bus 164. For an output operation the frame buffer/controller 116 receives processed vector data or vector processing parameters from the multi-processor 102 via data bus 162, address bus 164, then outputs the vector data or parameters to another programmable ultrasound signal processing apparatus 70 or another back-end processing subsystem.

Frame buffer/controller 116 includes respective registers 166, 168, 170. One register 166 passes raster data into the apparatus 70. Another register 168 passes vector data into or out of the apparatus 70, or vector processing parameters out of the apparatus 70. The third register 170 passes control signals to and from the ultrasound front end, or another back-end processing subsystem during a data transfer.

For raster data, a data frame passes through register 166 into either one or both of frame buffer A 172 and frame buffer B 174 via mux/demux 176, 178. A mux/demux 176, 178 in one embodiment is a D-type latch bus exchanger. A controller 180 determines the frame buffer 172, 174 and specific address within the selected frame buffer that a data item is to be stored. For raster data frames of a size to fit within a single frame buffer 172 or 174, sequential frames are loaded into alternating buffers 172, 174. For larger "over-sized" frames beyond the capacity of a single frame buffer 172 or 174, data initially is targeted for one frame buffer, then when the buffers fills, the excess is stored in the other frame buffer. For vector data, a data frame passes through register 168 into alternating frame buffers 172, 174.

Controller 180 configures the multiplexer/demultiplexer 176 to define the data path to be coupled to the frame buffer 172 at a given time. Data is loaded into frame buffer 172 from register 166, register 168 or multi-processor 102 data bus 162. Data is removed from frame buffer 172 to register 168 or multi-processor 102 data bus 162. Similarly, controller 180 configures the multiplexer/demultiplexer 178 to define the data path to be coupled to the frame buffer 174 at a given time. Data is loaded into frame buffer 174 from register 166, register 168 or multi-processor 102 data bus 162. Data is removed from frame buffer 174 to register 168 or multi-processor 102 data bus 162.

Each frame buffer 172, 174 is addressed by either the controller 180 or the multi-processor 102. A multiplexer 182 defines the address signal source for frame buffer 172. A multiplexer 184 defines the address signal source for frame buffer 174. Controller 180 selects the active address signal source channel at multiplexers 182, 184.

When a complete frame of data is received, controller 180 generates an interrupt to multi-processor 102. This signals multi-processor 102 to retrieve the frame for processing.

In a specific embodiment, echo data is received along one or more channels at an 18 MHz burst. The maximum burst per channel is referred to as a vector. In one embodiment, a vector can be up to 1024 12-bit echo depth samples and a frame can be up to 512 vectors of echo depth data. For scan-converted raster data, the maximum burst is a raster frame of converted vectors.

Frame Controller Modes: The apparatus 70 receives raster B-mode data, raster BC-mode data, vector B-mode data, or vector BC-mode data. The frame controller 180 operates in a primary mode or a secondary mode. In the primary frame controller mode raster data (e.g., B-mode or BC-mode) is received. In the secondary frame controller mode vector data (e.g., B-mode or BC-mode) is received.

For the primary mode, a B-mode raster data frame fits within a single frame buffer 172 or 174. A BC-mode raster data frame, however, requires either or both of the two frame buffers 172, 174. During a frame input, the controller 180 monitors the data header of incoming raster lines. The system controller 12 communicates to the controller 180 via VME interface 114 and multi-processor 102 specifying how many input channels are active. The controller 180 activates appropriate transceivers and generates address and control signals for storing the data in the frame buffer(s) 172, 174. Subsequent B-mode data frames are input into alternating frame buffers. Subsequent BC-mode data frames are input into alternating or the pair of frame buffers 172, 174 as the pair becomes available.

For the secondary mode, a vector data frame fits within a single frame buffer 172, 174. During a frame input, the controller 180 monitors the data header of incoming vectors. Once a vector header is detected, the data is routed from each active input channel (e.g., 1, 2 or 4 channels) to a select frame buffer 172, 174. The system controller 12 communicates to the controller 180 via VME interface 114 and multi-processor 102 specifying which input channels are active. The controller 180 activates appropriate transceivers and generates address and control signals for storing the data in the selected frame buffer 172, 174. Subsequent vector data frames are input into alternating frame buffers.

Output Buffer/Controller

Figure 8:
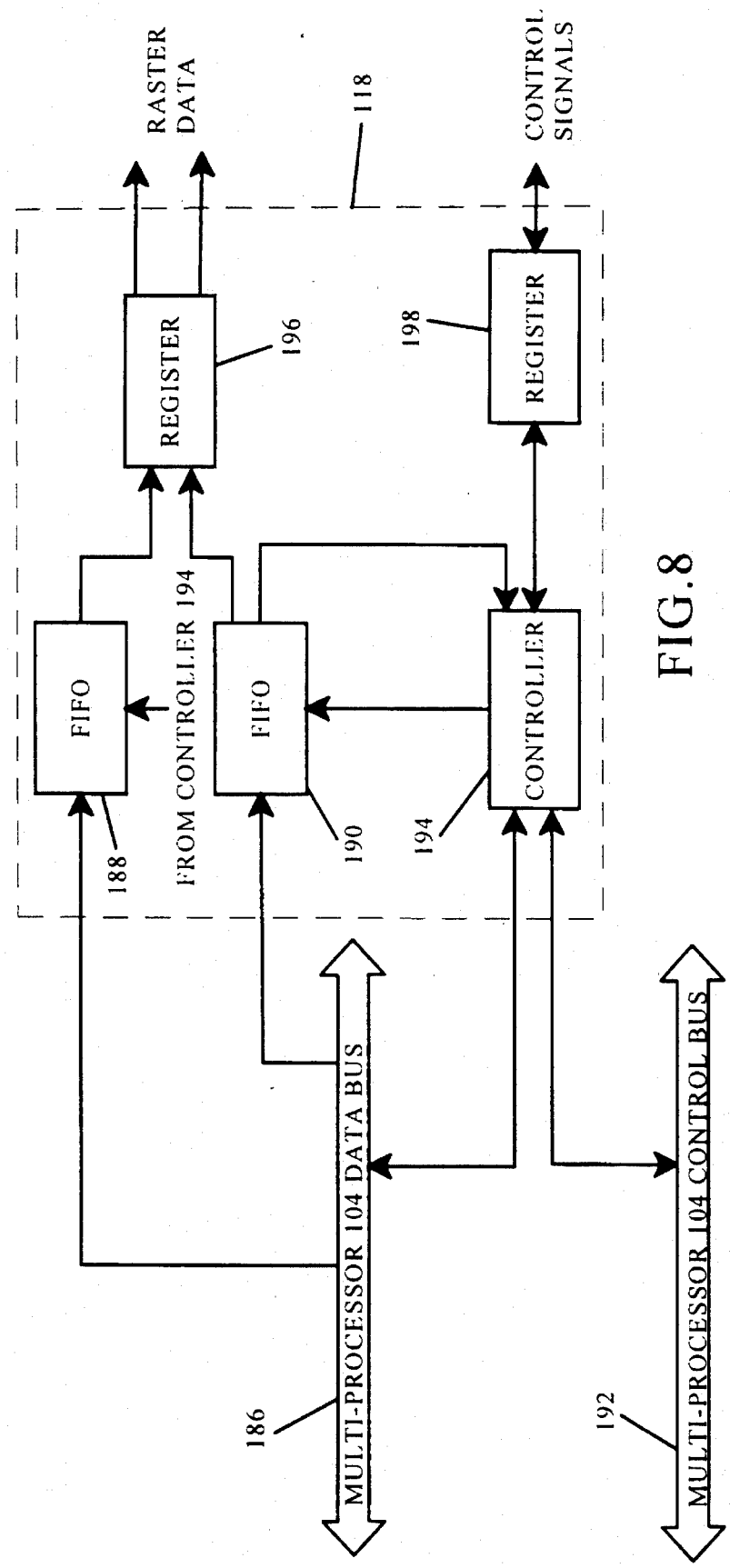
FIG. 8 is a diagram of the output buffer of FIG. 5.

The output buffer/controller 118 serves as a data interface between the apparatus 70 and another back-end processing subsystem (e.g., vector processing subsystem), or one or more output devices. FIG. 8 shows a block diagram of the output buffer/controller 118. Output data is received from the multi-processor 104 via data bus 186 at first-in first-out buffers 188, 190. Control data is received from multi-processor 104 via control bus 192 at controller 194. Multi-processor 104 loads lines of raster data into a FIFO 188, 190 by writing a data header followed by raster-coordinate data. At the end of the last raster line in a group loaded a tag value is written. The controller 194 detects the flag during subsequent output to identify the end of the group.

In one embodiment, the output buffer/controller 118 serves to buffer multiple lines (e.g., 4 lines) of raster data per window. Windows are then output in a burst mode to a video processing subsystem or directly to an output display device 32. The raster data is moved from the FIFOs 188, 190 into register 196. The raster data is output from register 196 on two channels with one channel transmitting even pixels, and the other channel transmitting odd pixels. The data bursts occurs either synchronously or asynchronously with a VSYNC signal according to the mode of operation.

The controller 194 begins moving data from FIFOs 188, 190 through register 196 out of the apparatus 70 when a FIFO 188,190 nears a first programmed level. FIFOs contain one or more raster lines. The controller 194 arbitrates for a system bus via register 198. When the bus is obtained, the controller 194 begins to burst raster data. Bus protocol is maintained by control signals transmitted/received at controller 194 via register 198. When the FIFO 188, 190 nears a second (lesser) programmed level, the controller 194 signals multi-processor 104 to begin loading another line of data. At some point during the output process, the controller 194 detects the end of window tag. In response, the controller 194 releases the bus at the end of the window and waits for multi-processor 104 to begin transferring the next window.

Scan Converter 70 Data Flow

Figure 9:
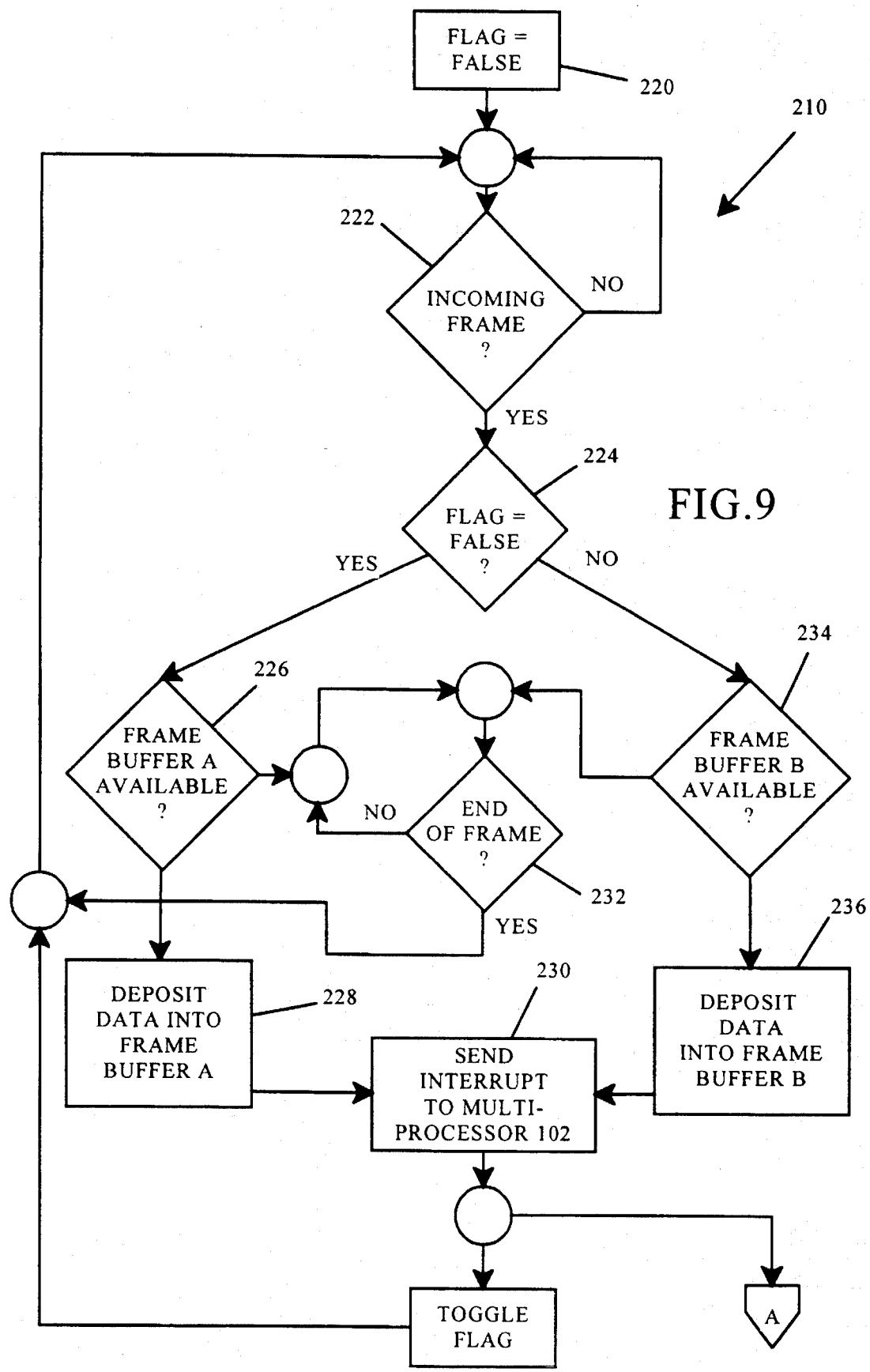
FIGS. 9–11 are flow charts of data movement through the scan conversion apparatus of FIG. 5.
Figure 10:
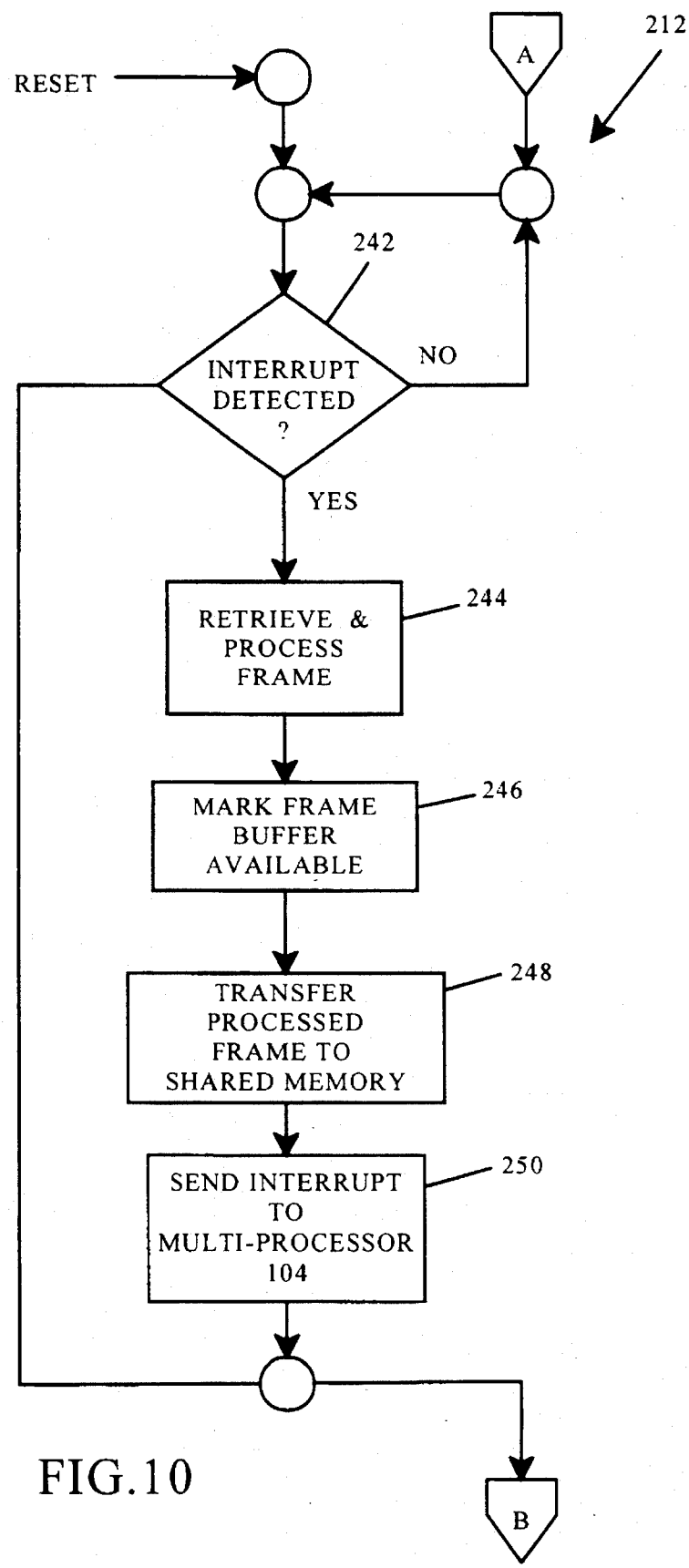
Figure 11:
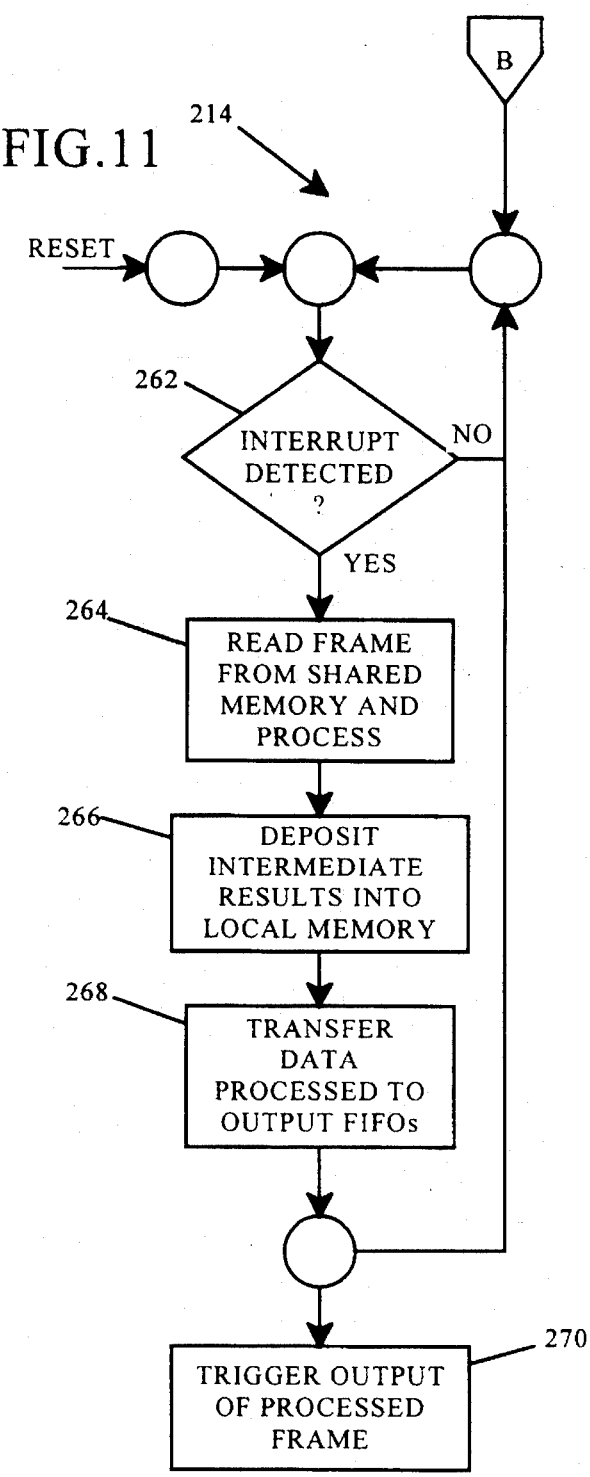

FIGS. 9–11 show flow charts depicting data movement through the scan converter apparatus 70. FIG. 9 depicts the frame controller's 180 process 210. FIG. 10 depicts the first multi-processor's 102 data flow process 212. FIG. 11 depicts the second multi-processor's 104 data flow process 214.

Referring to FIG. 9 the frame controller process 210 begins with a system reset or self reset of a FLAG at step 220. The frame controller 180 then awaits an incoming frame at step 222. When a frame is incoming, the controller 180 tests FLAG at step 224 to see if it is 'false'. If false, then the controller 180 tests frame buffer 'A' 172 to determine if available, (step 226). If available, then at step 228 the frame of data is deposited into frame buffer 'A'. If the frame does not fit within frame buffer 172, then the rest of the frame is deposited in frame buffer 174 when it becomes available. Once the entire frame is deposited into frame buffer 172(174), the controller 180 generates an interrupt to the first multi-processor 102 at step 230. This triggers the multi-processor 102 data flow process 212 of FIG. 10. Controller 180 then toggles FLAG to be 'true.'

If at step 226 frame buffer 172 was found to be unavailable, then the multi-processors 102, 104 are not keeping up with the data flow. In this situation imaging is performed in near real-time. The current frame then is dropped at step 232. Frame controller 180 then returns to step 222 and waits for another data frame.

Once an interrupt is sent to the multi-processor 102 and FLAG is set 'true,' controller 180 loops to step 222 and again waits for an incoming frame. Once the frame arrives, controller 180 performs step 224 testing FLAG. This time FLAG is 'true.' Thus, controller branches to step 234 where frame 'B' 174 is tested to see if available. If available, then at step 236 the frame of data is deposited into frame buffer B 174. If the frame does not fit within frame buffer 174, then the rest of the frame is deposited in frame buffer 172 when it becomes available. Once the entire frame is deposited into frame buffer 174(172), the controller 180 generates an interrupt to the first multi-processor 102 at step 230. This triggers the multi-processor 102 data flow process 212 of FIG. 10. Controller 180 then toggles FLAG to be 'false'.

If at step 234 frame buffer 174 was found to be unavailable, then the multi-processors 102, 104 are not keeping up with the data flow. Thus, the current frame is dropped at step 232. Controller 180 then returns to step 222 waiting for another data frame.

In this manner, sequential data frames are loaded alternatively in frame buffers 172 then 174 for frames of a size less than frame buffer capacity. For an over-sized frame, a first portion of the frame is loaded into one frame buffer, then the remaining portion is loaded into the other frame buffer.

Referring to FIG. 10, the first multi-processor 102 data flow process 212 begins with a reset. At step 242 multi-processor 102 waits for the interrupt from frame controller 180. Once the interrupt is detected and serviced, multi-processor 102 retrieves the frame from the frame buffer(s) 102, 104. The frame is moved into on-chip memory 136–144 and/or local memory 106, then processed at step 244. In one embodiment data processing is allocated between the first multi-processor 102 and second multi-processor 104. For example, for a given frame of data and a given active image area of 1000 groups of pixels, one-half of the groups are allocated to be processed by the DSPs of the first multi-processor 102, while the other half is allocated to be processed by DSPs of the second multi-processor 104.

At step 246 the multi-processor 102 marks the originating frame buffer as being available for reloading. At step 248 the processed frame data is moved to shared memory 112. At step 250, multi-processor 102 generates an interrupt at multi-processor 104. Multi-processor 102 then completes its data processing, then loops to step 242 to await the next interrupt so another frame of data can be processed.

Referring to FIG. 11, the second multi-processor 104 data flow process 214 begins with a reset. At step 262 multi-processor 104 waits for the interrupt from multi-processor 102. Once the interrupt is detected and serviced, multi-processor 104 reads its data in the frame from shared memory 112. The data is moved into on-chip memory 136–144 and/or local memory 108, and processed at step 264. During processing, intermediate results are stored in local memory 108 at step 266. At step 268 processed data is sent to the output buffer FIFOs 188, 190 (see FIG. 8). At step 270 multi-processor 104 signals the output buffer controller 194 to output the frame to another back end subsystem and/or output devices 32.

Distributed Scan Conversion Method

The scan conversion method includes vector identification, distance weighting and interpolation tasks. The interpolation tasks are performed for every frame to be scan converted. The vector identification and distance weighting tasks are performed as needed (i.e., in response to user changes to steering focus, image size, image shape or other parameter altering the active image area size shape and orientation).

Vector Identification

Vector identification processing includes identifying the active image area and correlating output pixel locations within the active image area to input vector samples. FIG. 2c shows an active image area 14. Such area 14 is formed by known pixels. Such pixels are to be illuminated at appropriate gray-scale levels to create the ultrasound image. The pixel addresses (i.e., locations) within the active image area are allocated into groups of output pixel addresses. These pixel addresses are stored in shared memory 112 within an output pixel address table 280 (See FIG. 14).

For each such output pixel address a set of input vector addresses is identified. Beam-formed data samples corresponding to such input vector addresses are interpolated to achieve the output pixel value (e.g., gray-scale intensity). The number and manner of selecting which input vector sample addresses to use varies according to the embodiment. According to one embodiment an n×m kernel is used, where n represents a number of vectors and m represent a number of ranges along a vector.

Figure 12:
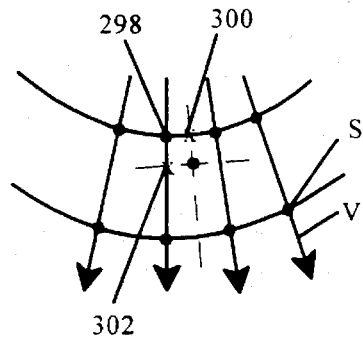
FIG. 12 is a diagram of an output pixel location relative to multiple input vector sample locations used in interpolating an output pixel value.

FIG. 12 depicts vector sample locations and an output pixel location for a 2×4 interpolation kernel. An output pixel location P within the active image area 14 is in the vicinity of several input vector sample locations S. Each vector sample S has a angular orientation θ and a range R. The angular orientation corresponds to a given vector V. For the 2×4 kernel 2 range locations for each of 4 nearest vectors are used as the vector address locations. The data value corresponding to each such vector point S is used to interpolate the display value for the pixel P. For every pixel location P in the active image area a set of n×m vector sample addresses S are derived and stored. Thus, for each group of output pixel addresses there is a corresponding group of n×m input vector addresses. These input vector addresses are stored in shared memory 112 within an input vector address table 282 (See FIG. 14).

Distance Weighting

For every pixel location P in the active image area 14, there is a set of offset distance weights calculated. The set includes weights for each of the corresponding n×m input vector addresses previously identified. In one embodiment a range offset value and vector offset value are derived between a pixel P and each sample S in the set. Referring to FIG. 12, the range offset between the output pixel P and the vector sample 298 is the distance from location P to a point 300 having the same range as vector sample location 298. The vector offset is the angular offset distance from location P to the vector from which sample location 298 is sampled. Range offset distance and vector offset distance are stored for each output pixel of each pixel group. The range offset distances are stored in shared memory 112 within an ROB (i.e., range offset byte) table 284 (See FIG. 14). Similarly, the vector offset distances are stored in shared memory 112 within a VOB (i.e., vector offset byte) table 286 (See FIG. 14).

Interpolation

The beam-former 24 generates frames of input vector data samples from ultrasound signals receive at the transducer 10 (See FIG. 2). Each frame is routed to the back-end processing subsystems 50. The scan conversion apparatus 70 receives a frame of input vector data at frame buffers 116. From there the input vector data is transferred into shared memory 112 (See FIG. 5). A frame of data is stored in an input vector data buffer 288 within shared memory 112 (See FIG. 14). The input vector data is stored within the buffer 288 according to the pre-computed groups 1-N. Input vector data corresponding to the output pixels in Group 1 are stored together. Input vector data corresponding to the output pixels in Group 2 are stored together. Similar storage occurs for each of N groups. Note that a given input vector data sample may be stored in multiple groups because such sample may be used for interpolating output pixels of different groups.

Figure 13:
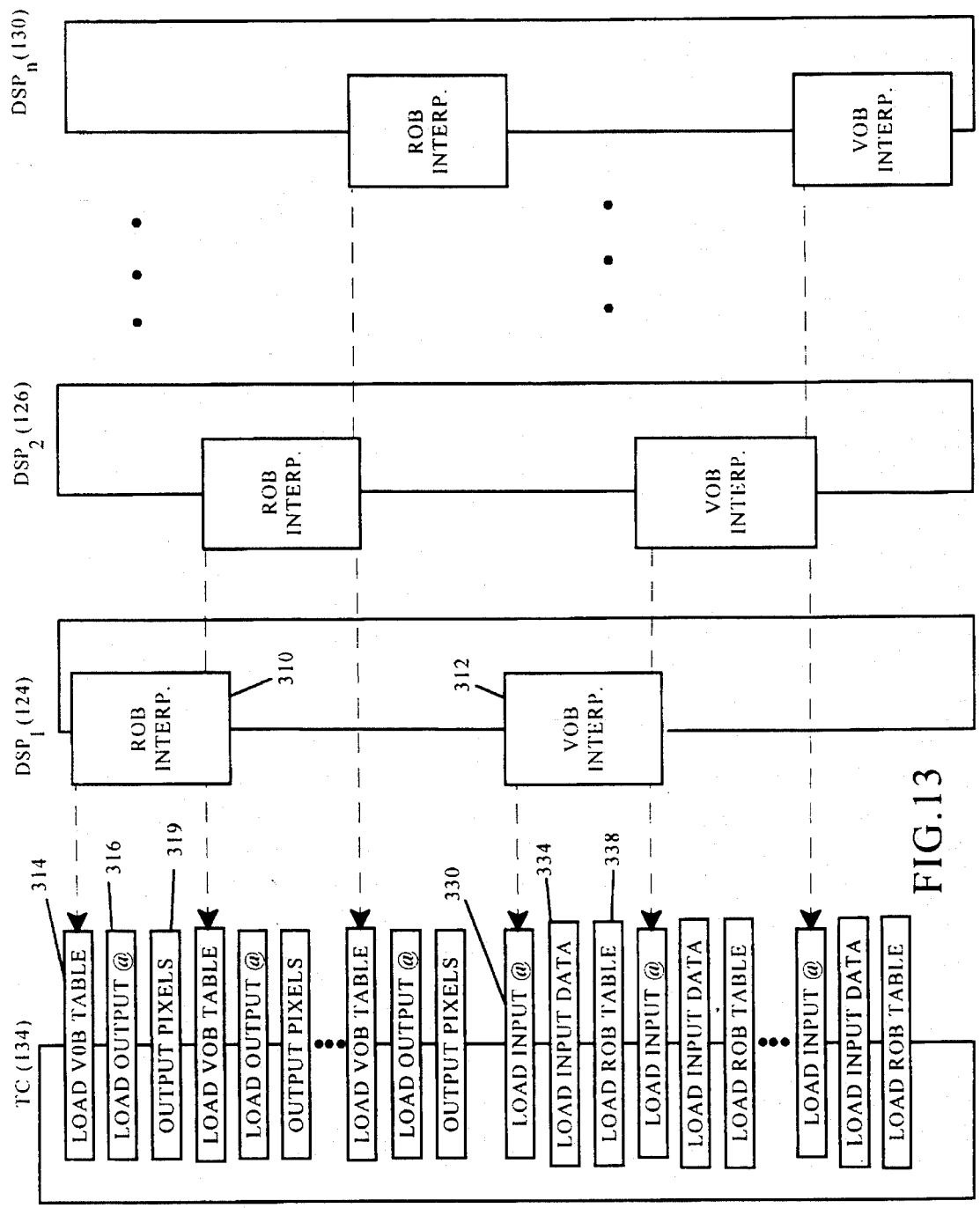
FIG. 13 is a flow chart of the interpolation processing tasks performed by the transfer controller and DSPs of FIG. 6 according to an embodiment of this invention.

FIG. 13 shows a flow chart of the interpolation processing according to an embodiment of this invention. As described above, the interpolation task is allocated among multiple processors 124-130. The processors execute in parallel. In one embodiment the interpolation processing at each processor is divided into range offset interpolation processing 310 and vector offset interpolation processing 312. Each processor 124-130 executes a loop interpolating one Group i of output pixels per cycle. For a 2 multi-processor 102,104 embodiment where there are eight digital signal processors each processor is allocated N/8 pixel groups to process. The transfer controller 134 for a given multi-processor 102/104 loads data into resident memory 136-144 (see FIGS. 6 and 14).

The transfer controller 134 processing responds to DSP requests for data. Thus, for each DSP cycle, the DSP 124 requests the transfer controller to bring in data for use during the following cycle. When such following cycle arrives, the data is present at the DSP 124's memory 136.

Figure 14:
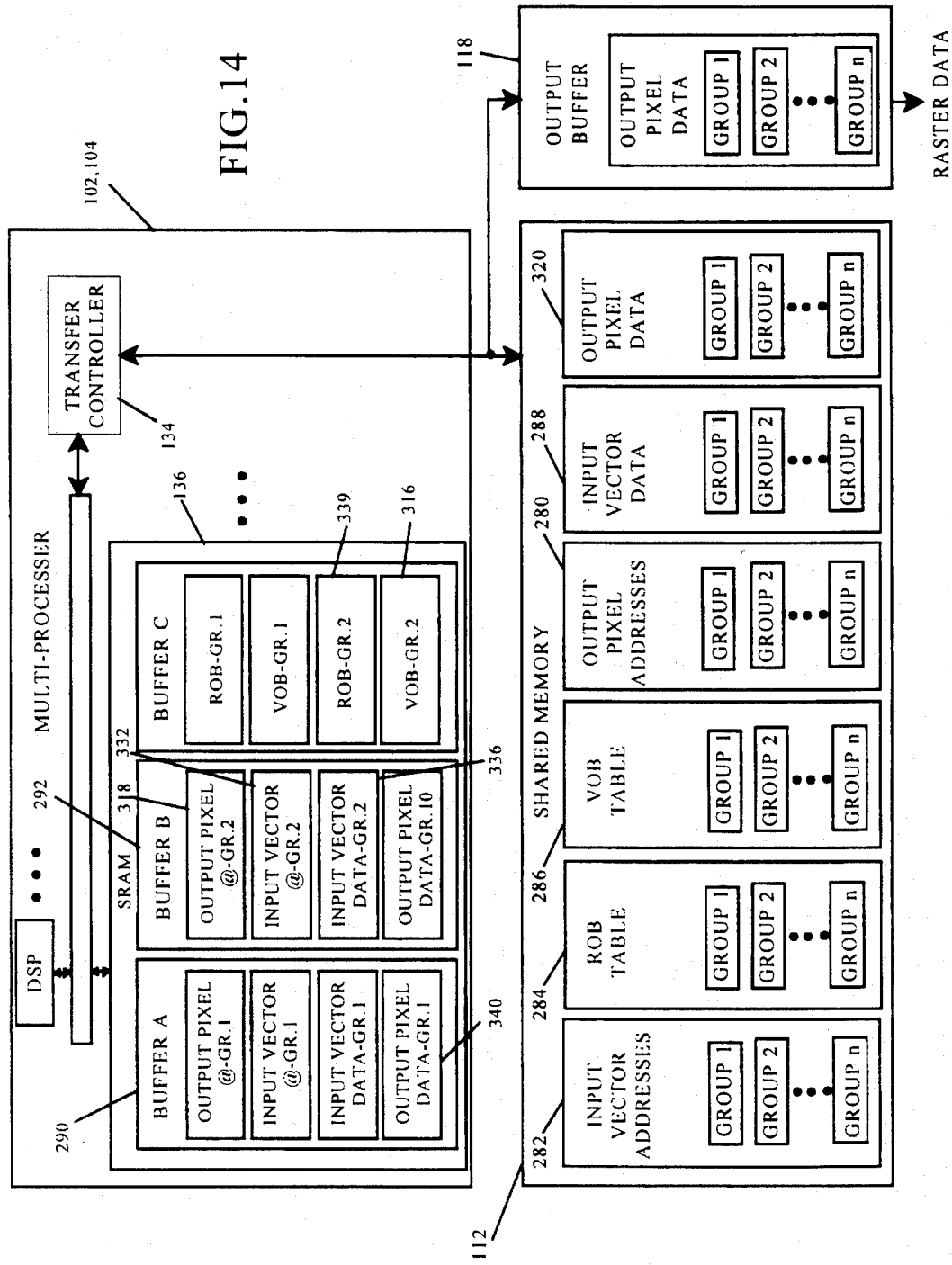
FIG. 14 is a diagram of data allocation and storage in the multi-processor(s), shared memory and output buffer of FIG. 5.

Referring to FIG. 14, consider DSP 124 beginning a cycle to interpolate output pixel data for Group 1. DSP 124 starts with the ROB interpolation processing 310, then performs VOB interpolation processing 312. During the prior cycle the DSP 124 requested the transfer controller 124 to load in the output pixel addresses, input vector addresses, input vector data, range offset distances and vector offset distances for Group 1. Such data is used for this cycle range offset interpolation processing 310 and vector offset interpolation processing 312. During each cycle, range interpolation is performed for each output pixel in the current group. According to one embodiment a distance weighted interpolation is executed. For the cycle i in which group 1 data is stored in buffer 290 (as shown in FIG. 14), the output pixel data values are stored in a portion of buffer 290. During each cycle, vector interpolation also is performed for each output pixel in the current group. According to one embodiment a multi-rate 128 tap filter is implemented. For the cycle in which group 1 data is interpolated, the output pixel data is stored in a portion 340 of buffer 290. Similar interpolation occurs at the other DSPs for other pixel groups.

During alternating cycles, the transfer controller 134, in ping-pong fashion stores the output pixel addresses, input vector addresses and input vector data in alternating buffers 290, 292. The range offset distance and vector offset distance data is stored in another buffer 294.

At the beginning of a cycle, the DSP 124 requests the transfer controller 134 to load in data for the next cycle. At step 314, the transfer controller 134 load in the VOB table for Group 2 from table 286 of shared memory 112 into the buffer 294 at portion 316. At step 316, the transfer controller 134 loads in the output pixel addresses for Group 2 from table 280 of shared memory into a portion 318 of the alternate buffer 292. At step 319, the transfer controller moves the output pixel data interpolated during the prior frame back into shared memory 112 at table 320 or directly into the output buffer 118. The transfer controller 134 performs similar steps for each of the other DSPs 126–130 in response to requests from such DSPs. As the transfers occur much faster than the interpolation, the transfer controller is able to move the data for each of the DSPs 124–130 without delay.

Once DSP 124 completes the range interpolation processing 310 for Group 1, vector offset interpolation processing 312 for Group 1 is executed. At the start, the DSP 124 requests the transfer controller 134 to load in the remaining data for the next cycle. At step 330, the transfer controller 134 loads the input vector addresses for Group 2 from table 282 of shared memory 112 into a portion 332 of alternate buffer 292. At step 334, transfer controller 134 loads the input vector data for Group 2 from table 288 of shared memory 112 into a portion 336 of alternate buffer 292. At step 338, the transfer controller 134 loads in the range offset distance data from for Group 2 from table 284 of shared memory 112 into a portion 339 buffer 294. The transfer controller 134 performs similar steps for each of the other DSPs 126–130 in response to requests from such DSPs. As the transfers occur much faster than the interpolation, the transfer controller is able to move the data for each of the DSPs 124–130 without delay.

During the next cycle, the DSP 124 alternates to use buffer 290 in place of 292 to store the data for Group 3, while the DSP 124 access the Group 2 data in buffer 292.

Meritorious and Advantageous Effects

One advantage of the scan conversion method of this invention is that a fast, efficient scan conversion occurs. Specifically, the complex nearest neighbor and square root functions executed for vector identification tasks are isolated from the interpolation tasks. Another advantage is that processing is reduced by avoiding interpolation for background points. Processing also is reduced by not having to perform blanking and bound checking for every pixel.

Although a preferred embodiment of the invention is illustrated and described, various alternatives also are used. For example, although a MVP chip is described as a specific multi-processor embodiment, other multi-processors or multiple stand-alone processors may be used. Similarly, although a distance weighted algorithm is used for range interpolation and a multi-rate 128 tap filter is used for vector interpolation, the interpolation algorithms and filters vary for differing embodiments. Although the output buffers are described as first-in first-out buffers, other stack buffers, frame buffers or window buffers may be used. Similarly, the various memory capacities, buffer capacities and transfer rates may vary. The disclosed architecture is scalable.

Therefore, the foregoing description should not be taken as limiting the scope of the inventions which are defined by the appended claims.

What is claimed is:

1. A method of scan converting ultrasound input vector data into raster image data, comprising the steps of:

identifying an active image area and a background area for an ultrasound image on a display screen, the active image area comprising a plurality of active-area pixels, the background area comprising a plurality of background-area pixels;

allocating only the active-area pixels among N multiple pixel groups;

for each one active-area pixel, determining a set vector sample locations for use in interpolating a corresponding pixel value;

for said each one active-area pixel, deriving a set of offsets for use in interpolating the corresponding pixel value, wherein there is an offset in the set of offsets for each vector sample location in the active-area pixel's corresponding set of vector sample locations;

wherein said steps of identifying, allocating, determining and deriving are repeated only upon a change of any one or more of the active image area shape, size, zoom or orientation;

loading by a controller into local memory of a first processor (i) active-area pixel locations for a first pixel group, (ii) the sets of vector sample locations corresponding to the active-area pixels of the first pixel group, and (iii) the sets of offsets corresponding to the active-area pixels of the first pixel group;

after said step of loading, interpolating at the first processor active-area pixel values for multiple pixel groups, an active-area pixel value being interpolated for each active-area pixel within a given pixel group based upon the active-area pixel's corresponding set of offsets and based upon input vector sample data for the active-area pixel's corresponding set of vector sample locations; and wherein said controller and first processor execute in parallel with said first processor cyclically performing the step of interpolating for a current one of multiple pixel groups while said controller performs the step of loading for a next-to-be current group, the controller loading into local memory of the first processor (i) active-area pixel locations for a the next-to-be current pixel group, (ii) the sets of vector sample locations corresponding to the active-area pixels of the next-to-be current pixel group, and (iii) the sets of offsets corresponding to the active-area pixels of the next-to-be current pixel group.

2. The method of claim 1, in which there a plurality of processors, one of said plurality of processors comprising the first processor, and further comprising the step of allocating the N pixel groups among the plurality of processors, each one processor performing interpolation for a unique pixel group in parallel with each of the other processors of the plurality of processors and in parallel with the controller performing of the loading step;

and wherein the controller loads into local memory of each one processor (i) active-area pixel locations for a next-to-be current pixel group for said each one processor, (ii) the sets of vector sample locations corresponding to the active-area pixels of the next-to-be current pixel group for said each one processor, (iii) and the sets of offsets corresponding to the active-area pixels of the next-to-be current pixel group for said each one processor.

3. The method of claim 2, in which the controller and plurality of processors form an integrated multi-processor.

4. The method of claim 1, in which the set of offsets weights for an active-area pixel comprises a range offset and a vector offset of the active-area pixel relative to a vector sample location for each vector sample location in the active-area pixel's corresponding set of vector sample locations.

* * * * *